US012758499B2

(12) United States Patent
Pereira De Brito et al.

(10) Patent No.: US 12,758,499 B2
(45) Date of Patent: Oct. 13, 2026

(54) PLASMA COATING METHOD OF NANOVESICLE SURFACE AND PLASMA JET DEVICE FOR PLASMA COATING OF NANOVESICLE SURFACE

(71) Applicants: Research & Business Foundation SUNGKYUNKWAN UNIVERSITY, Suwon-si (KR); AJOU UNIVERSITY INDUSTRY-ACADEMIC COOPERATION FOUNDATION, Suwon-si (KR)

(72) Inventors: Ana Sofia Pereira De Brito, Suwon-si (KR); Byeong Moon Kwak, Suwon-si (KR); Bum Ho Bin, Suwon-si (KR); Hyo Jin Heo, Suwon-si (KR); Byung Sun Cha, Suwon-si (KR); So Min Lee, Suwon-si (KR); So Young Jung, Suwon-si (KR); Lei Lei, Suwon-si (KR); Sang Hun Lee, Suwon-si (KR); Byung Mook Weon, Suwon-si (KR)

(73) Assignees: RESEARCH & BUSINESS FOUNDATION SUNGKYUNKWAN UNIVERSITY, Suwon-si (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 168 days.

(21) Appl. No.: 18/762,860

(22) Filed: Jul. 3, 2024

(65) Prior Publication Data

US 2025/0009661 A1 Jan. 9, 2025

(30) Foreign Application Priority Data

Jul. 3, 2023 (KR) ........................ 10-2023-0086012

(51) Int. Cl.
*A61K 9/1271* (2025.01)
*B01J 19/08* (2006.01)

(52) U.S. Cl.
CPC ........... *A61K 9/1271* (2013.01); *B01J 19/087* (2013.01)

(58) Field of Classification Search
CPC ............................ A61K 9/1271; B01J 19/087
See application file for complete search history.

(56) References Cited

FOREIGN PATENT DOCUMENTS

KR 10-2020-0128501 A 11/2020
KR 102815338 B1 * 5/2025

OTHER PUBLICATIONS

Mun et al, Direct Nanoparticle Coating Using Atmospheric Plasma Jet, J. Nanopart. Res. pp. 135-146. (Year: 2020).*

(Continued)

*Primary Examiner* — Carlos A Azpuru
(74) *Attorney, Agent, or Firm* — LEX IP MEISTER, PLLC

(57) ABSTRACT

An embodiment of the disclosure provides a plasma coating method of a nanovesicle surface and a plasma jet device for plasma coating of a nanovesicle surface. The plasma coating method of a nanovesicle surface according to an embodiment of the disclosure may be provided as a simple method for changing the surface charge of a nanovesicle from negative to neutral by utilizing the characteristic that when a neutral object meets a negatively charged object, electrons of the neutral object repel electrons of the negatively charged object and the negatively charged object becomes positively charged.

7 Claims, 5 Drawing Sheets

(56) References Cited

OTHER PUBLICATIONS

Yang et al. , Optimization of critical parameters for coating of polymeric nanoparticles with plasma membrane vesicles by sonication, Nature.com, Scientific Reports, 11:23996 (Year: 2023).*
Saito et al., nanomaterial Synthesis Using Plasma Generation in Liquids, Journal of Nanomaterials, vol. 2015,Artile ID 123696, 21 pages (Year: 2015).*

* cited by examiner

【FIG 1】
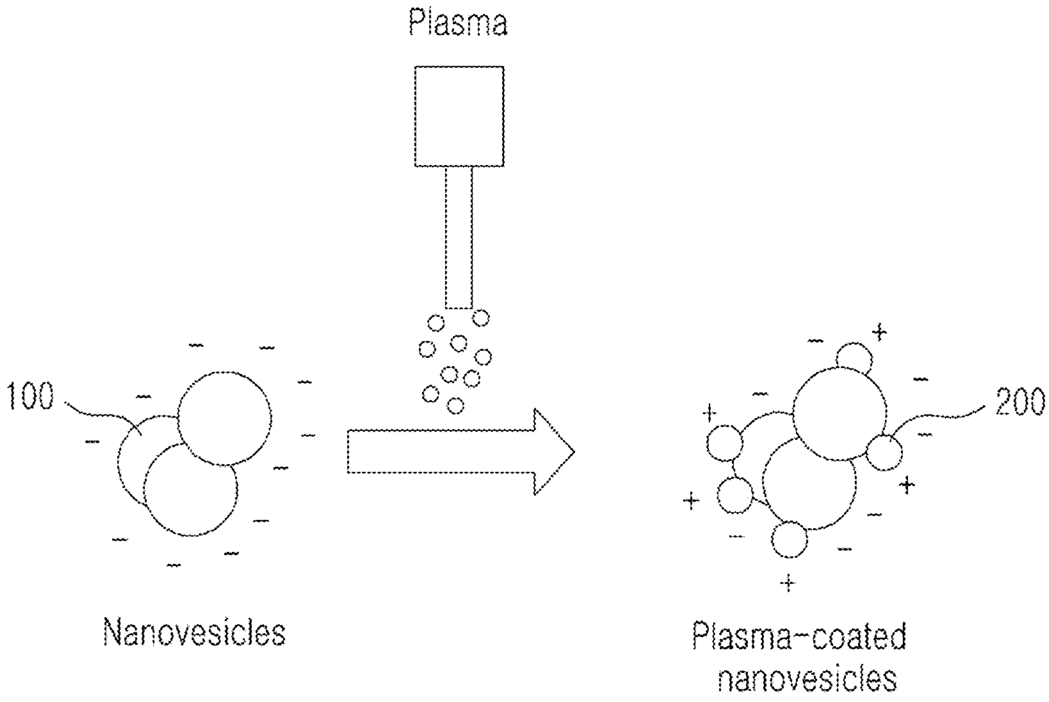

【FIG 2】
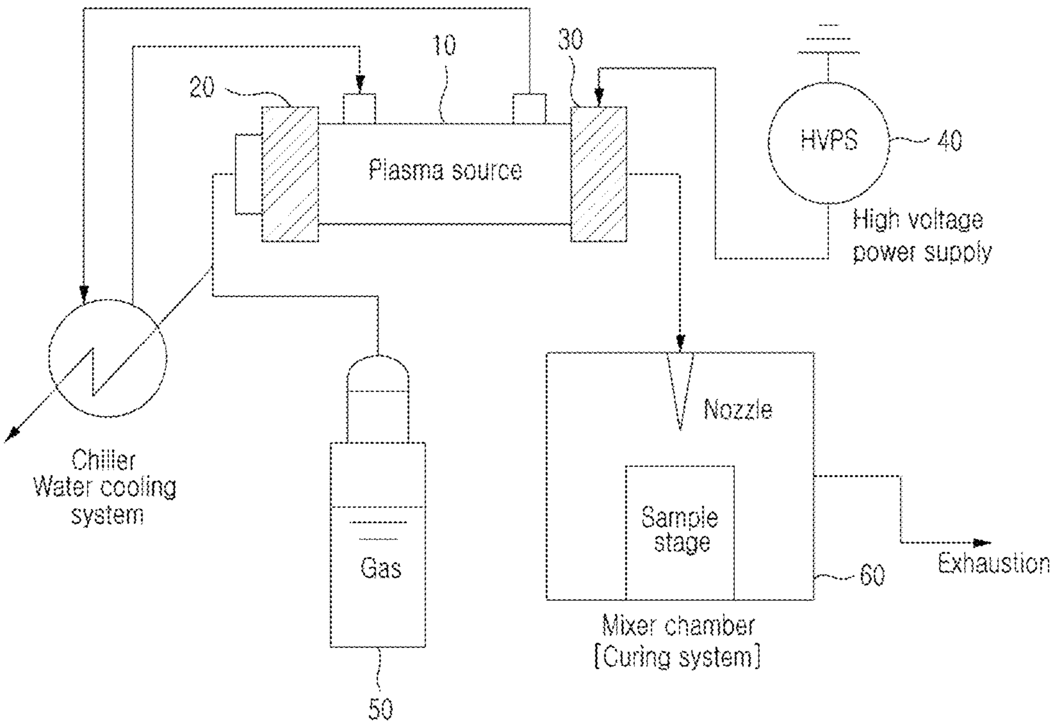

【FIG 3】
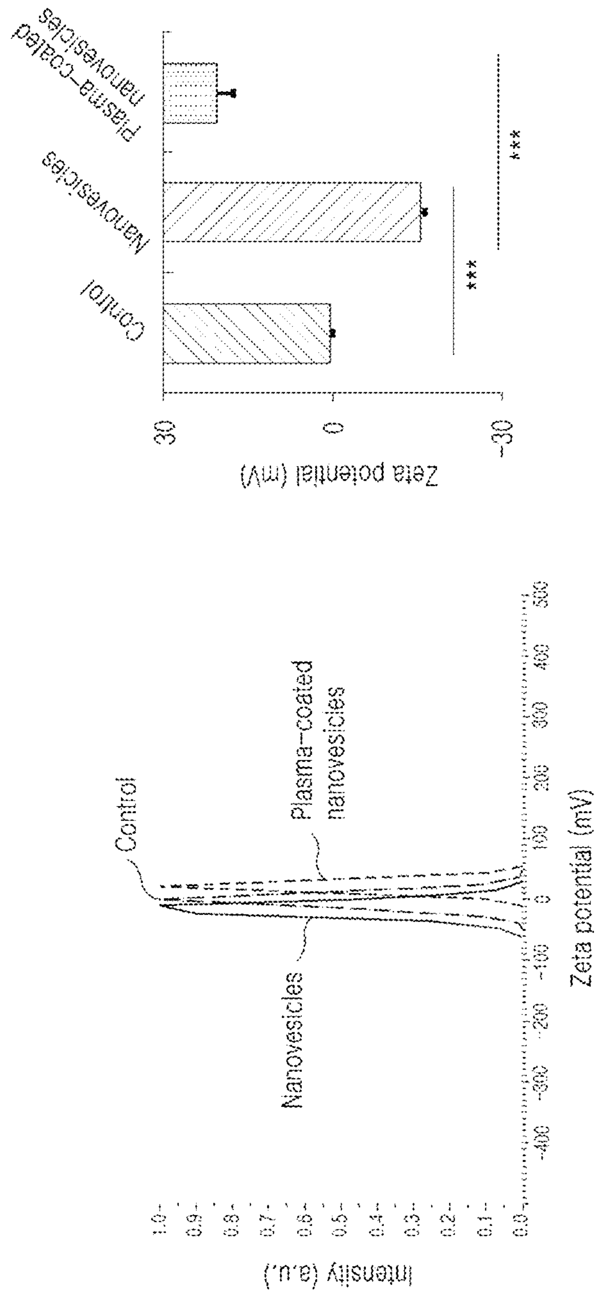

【FIG 4】
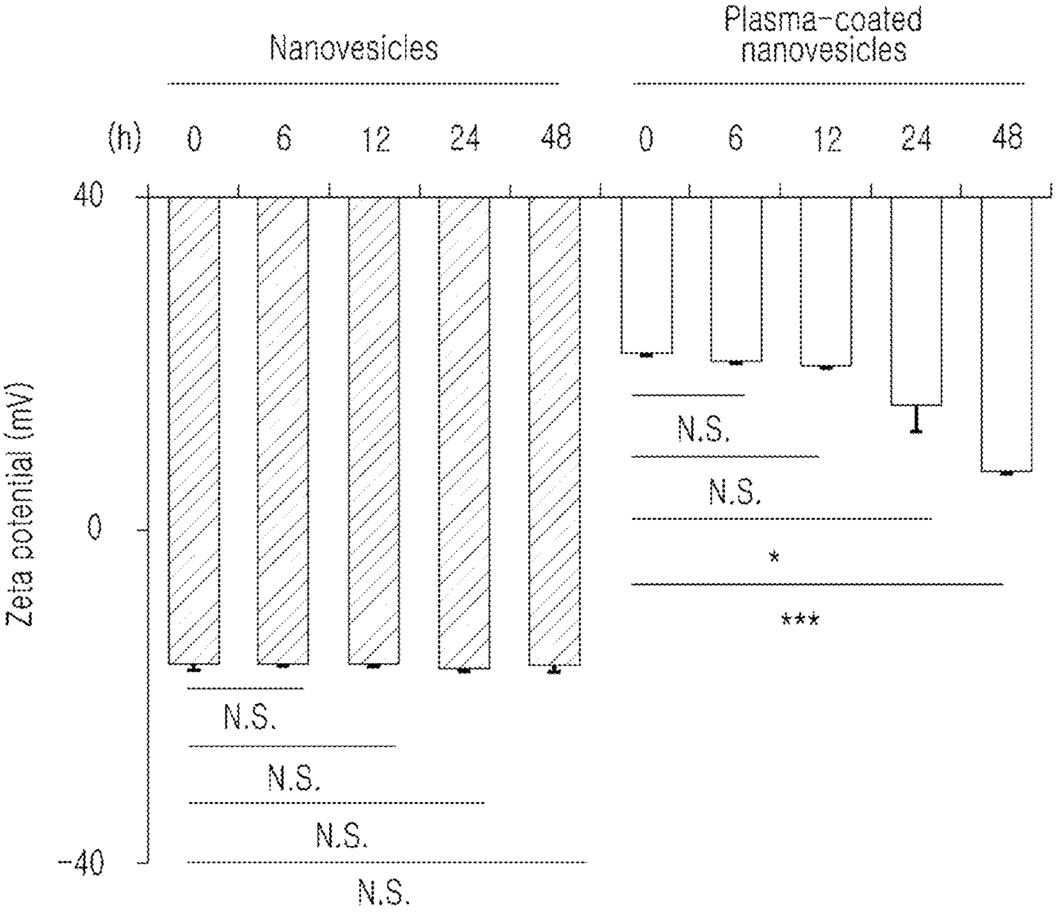

【FIG 5】
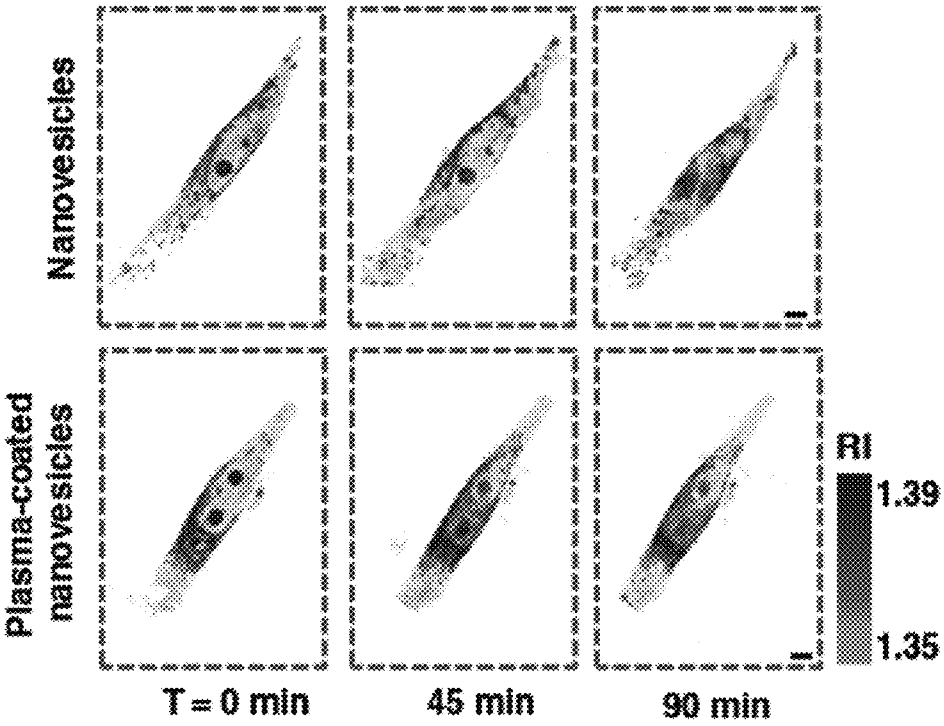
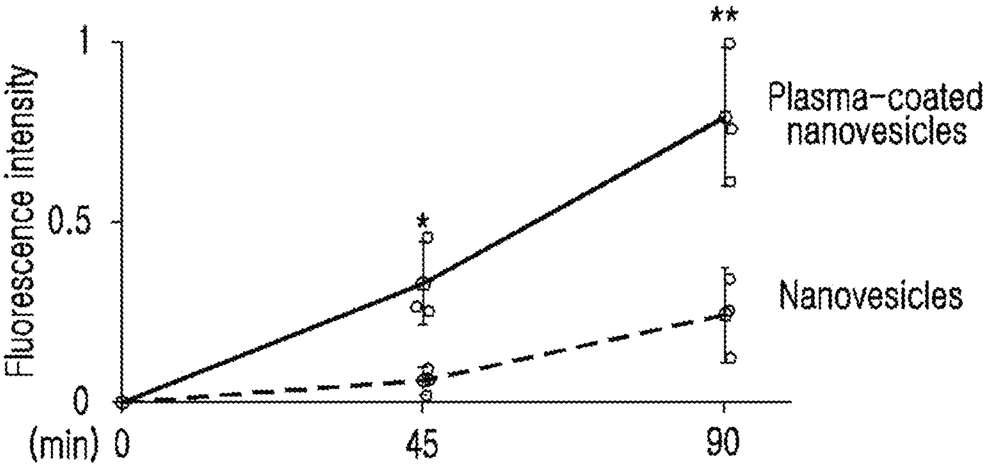

PLASMA COATING METHOD OF NANOVESICLE SURFACE AND PLASMA JET DEVICE FOR PLASMA COATING OF NANOVESICLE SURFACE

CROSS-REFERENCE TO RELATED APPLICATION

This application claims priority to Korean Patent Application No. 10-2023-0086012, filed on Jul. 3, 2023, in the Korean Intellectual Property Office, the entire disclosures of which are incorporated herein by reference for all purposes.

BACKGROUND

The disclosure relates to a plasma coating method of a nanovesicle surface and a plasma jet device for plasma coating of a nanovesicle surface.

Nanovesicles are cell-derived biological systems with high potential for delivering drugs or other biomolecules into the body.

Previous studies have demonstrated the ability of nanovesicles in cancer treatment by transporting chemotherapy to cancer cells as well as in regenerative medicine that helps cell proliferation and tissue regeneration.

One of the greatest advantages of these systems is that it is possible to prevent long-term exposure and high concentrations of drug treatments that may generally cause cell damage and system toxicity.

However, one of the existing challenges of nanovesicle therapy is increasing permeability.

Since the nanovesicles have a large amount of negative charge on their surface, the negative charge causes an unbalanced electrostatic interaction with the cell membrane, and the resulting electron repulsion inhibits cell penetration, resulting in a decrease in therapeutic efficacy.

Various methods have been attempted to alleviate this problem, including modifications to the size, shape, charge, and hydrophilicity of the nanoparticles, but no effective solution has been proposed so far.

Therefore, there is a need to design a new solution for nanovesicle therapy that can overcome this problem and be applied clinically.

SUMMARY

An aspect of the disclosure is to provide a plasma coating method of a nanovesicle surface, which is capable of modifying the surface charge of a nanovesicle by applying neutral charge plasma, and a plasma jet device for plasma coating of a nanovesicle surface.

The aspect of the disclosure is not limited to that mentioned above, and other aspects not mentioned will be clearly understood by those skilled in the art from the description below.

An embodiment of the disclosure provides a plasma coating method of a nanovesicle surface.

According to an embodiment of the disclosure, a plasma coating method of a nanovesicle surface comprises: preparing a mixture by dissolving nanovesicles in a phosphate buffered saline (PBS) solution; injecting the mixture containing the nanovesicles into a plasma jet device; and applying a preset voltage to the plasma jet device and performing plasma coating on the surface of the nanovesicles under preset gas flow conditions.

In addition, according to an embodiment of the disclosure, in the performing of the plasma coating on the surface of the nanovesicles, the charge on the surface of the nanovesicles may be converted from negative to neutral.

In addition, according to an embodiment of the disclosure, in the preparing of the mixture, the content of the nanovesicles in the mixture may be 1 wt % to 99.99 wt % of the total mixture.

In addition, according to an embodiment of the disclosure, in the preparing of the mixture, the concentration of the PBS solution in the mixture may be 0.001 M to 1 M.

In addition, according to an embodiment of the disclosure, in the performing of the plasma coating on the surface of the nanovesicles, the applied voltage for generating plasma may be 1 kW to 50 kW.

In addition, according to an embodiment of the disclosure, in the performing of the plasma coating on the surface of the nanovesicles, an applied frequency for generating plasma may be 1 kHz to 100 KHz.

In addition, according to an embodiment of the disclosure, in the performing of the plasma coating on the surface of the nanovesicles, the flow rate of gas applied in the plasma coating process may be 1 ccm/min to 50 ccm/min.

Another embodiment of the disclosure provides a plasma jet device for plasma coating of a nanovesicle surface.

According to an embodiment of the disclosure, the plasma jet device for plasma coating of a nanovesicle surface may include: a plasma source device; a first electrode arranged on one side of the plasma source device; a second electrode arranged on one side of the plasma source device and oriented toward the first electrode; a plasma power device connected to the plasma source device to generate plasma; a gas input device connected to the first electrode or the second electrode of the plasma source device to inject gas thereinto; and a chamber composed of a nozzle connected to one of the first electrode or the second electrode, and a plasma deposition stage, wherein plasma generated by the plasma source device and the plasma generation device is injected through the nozzle to form plasma coating on the surface of a nanovesicle positioned on the plasma deposition stage.

In addition, according to an embodiment of the disclosure, one side of an electrode not connected to the nozzle among the first and second electrodes may be formed as a dielectric layer.

In addition, according to an embodiment of the disclosure, as for the nanovesicle injected into the chamber, a mixture of nanovesicles dissolved in a phosphate buffered saline (PBS) solution may be injected.

In addition, according to an embodiment of the disclosure, the plasma source comprises at least one selected from the group consisting of $N_2$, $O_2$, OH, $H_2O_2$, and $O_3$.

In addition, according to an embodiment of the disclosure, the charge on the surface of the nanovesicle may be converted from negative to neutral by the plasma jet device.

The plasma coating method of a nanovesicle surface according to an embodiment of the disclosure may be provided as a simple method for changing the surface charge of a nanovesicle from negative to neutral by utilizing the characteristic that when a neutral object meets a negatively charged object, electrons of the neutral object repel electrons of the negatively charged object and the negatively charged object becomes positively charged.

In addition, a surface-modified nanovesicle according to an embodiment of the disclosure have an effect of converting the surface charge to neutral, thereby facilitating intracellular penetration, and consequently enhancing the delivery efficiency for target drug delivery and other clinical applications.

The effects of the disclosure are not limited to the effects described above, and should be understood to include all effects that are inferable from the configuration of the disclosure described in the detailed description or claims of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 is a schematic diagram showing a plasma coating method of a nanovesicle surface according to an embodiment of the disclosure;

FIG. 2 is a schematic diagram showing a plasma jet device for plasma coating of a nanovesicle surface according to an embodiment of the disclosure;

FIG. 3 is a graph showing the effectiveness of a plasma coating method according to an embodiment of the disclosure;

FIG. 4 is a graph showing the overtime effect of a plasma coating method according to an embodiment of the disclosure; and FIG. 5 is an exemplary diagram showing the improved cell affinity characteristics of a plasma coating method according to an embodiment of the disclosure.

DETAILED DESCRIPTION

Hereinafter, preferred embodiments of the disclosure, which may specifically achieve the aspects as described above, are described with reference to the accompanying drawings. In describing these embodiments, the same names and symbols may be used for the same components, and additional descriptions thereof may be omitted.

A plasma coating method of a nanovesicle surface according to an embodiment of the disclosure will be described.

FIG. 1 is a schematic diagram showing a plasma coating method of a nanovesicle surface according to an embodiment of the disclosure.

Referring to FIG. 1, a method for plasma coating on a nanovesicle surface according to an embodiment of the disclosure may include: preparing a mixture by dissolving nanovesicles in a phosphate buffered saline (PBS) solution; injecting the mixture containing the nanovesicles into a plasma jet device; and applying a preset voltage to the plasma jet device and performing plasma coating on the surface of the nanovesicles under preset gas flow conditions.

As a first step, preparing a mixture by dissolving nanovesicles in a phosphate buffered saline (PBS) solution may be included. (S100)

Nanovesicles refer to nanometer-sized vesicles, and thus various technologies are being developed to deliver drugs through the nanovesicles and thereby reduce systemic toxicity.

At this time, the nanovesicles are characterized by having a negative charge, and when the nanovesicles have a negative charge on the surface, there is a problem of showing low intracellular affinity.

Accordingly, in the disclosure, it is possible to use plasma treatment to solve the problem that the surface of the nanovesicles has a negative charge.

At this time, the disclosure may be applied to all types of negatively charged nanovesicles. Application examples include lipid-based nanovesicles such as exosomes and liposomes.

In order to modify the surface of the nanovesicles by plasma treatment in the disclosure, the disclosure is characterized by preparing a mixture by dissolving nanovesicles in a PBS solution.

At this time, the content of the nanovesicles in the mixture includes 1 wt % to 99.99 wt % of the total mixture.

At this time, as for the nanovesicles, an undiluted original solution is used.

At this time, when the content of the nanovesicles of the disclosure exceeds 60 wt %, a peculiar odor may occur, but the odor is harmless to the human body.

In addition, the concentration of the PBS solution in the mixture of the disclosure is 0.001 M to 1 M.

At this time, the phosphate buffered saline (PBS) is a buffer solution that may not only buffer but also adjust osmolality (osmotic pressure), and thus may produce a buffer solution closest to the ion concentration (pH 7.4) and osmotic pressure in the body.

At this time, when the process is performed by dissolving the negative charge of the nanovesicles in phosphate buffered saline (PBS), the negative charge on the surface changes significantly to the positive charge, which may lead to better neutralization. This is because the pH is maintained constant by the osmotic pressure of the PBS, thereby increasing cell permeability and increasing the possibility of shifting to a positive ion during plasma coating.

At this time, in the disclosure, not only PBS but also HEPES buffer or HBSS buffer may be used as the mixture, and any substance with similar buffer properties to the intracellular ion concentration and osmotic pressure may be used.

As a second step, injecting the mixture containing the nanovesicles into a plasma jet device may be included. (S200)

At this time, the mixture including the nanovesicles may be included inside a chamber of a plasma jet device described later.

As a third step, applying a preset voltage to the plasma jet device and performing plasma coating on the surface of the nanovesicles under preset gas flow conditions may be included. (S300)

A plasma source for the plasma coating may include at least one selected from the group consisting of $N_2$, $O_2$, OH, $H_2O_2$, and $O_3$.

Specifically, Ar, He, and Ne may be further included as a plasma source to generate positive ion plasma, and any case of materials capable of neutralizing a negatively charged nanovesicle through plasma coating may be used without limitation without being limited to the above-described materials.

For example, the disclosure may use $N_2$ as a plasma source to perform nitrogen plasma treatment.

At this time, the plasma generation applied voltage for the plasma coating is 1 kW to 50 kW.

At this time, the plasma generation applied voltage may be used without limitation as long as this is a voltage capable of performing plasma coating on the surface of nanovesicles.

In addition, the applied frequency for plasma generation is 1 kHz to 100 kHz.

At this time, the plasma generation frequency may be used without limitation if this is a frequency capable of performing plasma coating on the surface of nanovesicles.

In addition, the flow rate of gas applied in the plasma coating process is 1 ccm/min to 50 ccm/min.

At this time, the gas flow rate applied in the plasma coating process may be used without limitation if this is a gas flow rate enabling to perform plasma coating on the surface of nanovesicles.

A method for performing plasma coating on the surface of a nanovesicle according to an embodiment of the disclosure applies neutral charge plasma to change the surface charge of nanovesicles.

Specifically, when a neutral object meets a negatively charged object, electrons of the neutral object repel electrons of the negatively charged object, and the negatively charged object may become positively charged.

Referring to FIG. 1, when plasma is applied to a neutral nanovesicle, it is possible to confirm that a positive charge is attached, and it is possible to confirm that the entire nanovesicle is neutral due to the attached positive charge.

At this time, the proof for the specific plasma treatment time, applied voltage, and applied frequency will be described later in the experimental example below.

A plasma jet device for plasma coating of a nanovesicle surface according to another embodiment of the disclosure will be described.

Referring to FIG. 2, a plasma jet device for plasma coating of a nanovesicle surface according to an embodiment of the disclosure may include: a plasma source device 10; a first electrode 20 arranged on one side of the plasma source device; a second electrode 30 arranged on one side of the plasma source device and oriented toward the first electrode; a plasma power device 40 connected to the plasma source device to generate plasma; a gas input device 50 connected to the first electrode or the second electrode of the plasma source device to inject gas thereinto; and a chamber 60 composed of a nozzle connected to one of the first electrode or the second electrode, and a plasma deposition stage, wherein plasma generated by the plasma source device and the plasma generation device is injected through the nozzle to form plasma coating on the surface of a nanovesicle positioned on the plasma deposition stage.

The disclosure may include a plasma source device 10.

The plasma source device is particularly useful for generating a high-charge particle density source of chemically active species, electrons, and ions to provide various plasma-related processes requiring high power density.

Accordingly, the plasma source device in the plasma jet device of the disclosure may be used without limitation in form if this generates a plasma in which electrons, ions, and neutral species are separated from the injected plasma source by applying a lot of energy and electrodes may be positioned at both ends.

At this time, the plasma source may include at least one selected from the group consisting of $N_2$, $O_2$, OH, $H_2O_2$, and $O_3$.

The disclosure may include a first electrode 20.

At this time, the first electrode is arranged on one side of the plasma source device.

At this time, the first electrode may be composed of at least one material selected from the group consisting of aluminum, nickel, gold, silver, copper, silicon dioxide, aluminum oxide, and titanium oxide, and any material having conductive properties may be used without limitation.

The disclosure may include a second electrode 30.

At this time, the second electrode is arranged on one side of the plasma source device and is oriented to the first electrode.

At this time, the second electrode may be composed of at least one material selected from the group consisting of aluminum, nickel, gold, silver, copper, silicon dioxide, aluminum oxide, and titanium oxide, and any material having conductive properties may be used without limitation.

At this time, one side of an electrode not connected to the nozzle among the first electrode and the second electrode is formed as a dielectric layer.

At this time, the dielectric layer may be composed of a ceramic dielectric layer.

The disclosure may include a plasma power device 40.

The plasma power device is connected to a plasma source device to generate plasma, and any device capable of generating plasma may be used without limitation.

The disclosure may include a gas input device 50.

At this time, the gas input device is connected to a first electrode or a second electrode of the plasma source device to inject gas thereinto, and any device capable of injecting gas may be used without limitation.

The disclosure may include a chamber 60.

At this time, the chamber may include a nozzle connected to one of the first electrode or the second electrode of the plasma source device and a nanovesicle sample for coating plasma.

At this time, the nanovesicle sample is a mixture in which nanovesicles are dissolved in a phosphate buffered saline (PBS) solution.

At this time, the nanovesicle sample is a mixture obtained by dissolving nanovesicles in a phosphate buffered saline (PBS) solution, and is replaced with the description of the plasma coating method of a nanovesicle surface described above.

At this time, the charge on the surface of the nanovesicles is converted from a negative charge to a positive charge by the plasma jet device.

Hereinafter, the disclosure will be described in more detail through a production example and an experimental example. These production example and experimental example are only intended to illustrate the disclosure, and the scope of the disclosure is not limited by these production example and experimental example.

Production example 1: Plasma coating method of nanovesicle surface

First, 40 μg of nanovesicles were dissolved in a phosphate buffered saline (PBS) 1 ml solution to prepare a mixture.

Next, the mixture including the nanovesicles was introduced into a plasma coating device.

Next, a microcentrifuge tube including nanovesicles diluted in PBS was placed on a stage of a plasma jet device, and a nozzle was placed 0.5 cm away from the solution. Then, plasma coating was performed on the nanovesicles by injecting nitrogen plasma at a constant flow rate for 10 minutes while fixing the gas flow rate at 225 V.

At this time, a plasma source used a power of 5 kW and 30 kHz, and cooling was performed by a water flow flowing around the source.

In addition, the plasma was injected by a common gas flow in a mixer chamber of 135,200 mm3.

Experimental example: Nanovesicle surface plasma coating confirmation and characteristic confirmation Referring to FIGS. 3 to 5, the plasma coating characteristics of a nanovesicle surface will be described.

FIG. 3 is a graph showing the effectiveness of a plasma coating method according to an embodiment of the disclosure.

Referring to FIG. 3, the results of confirming a plasma zeta potential value show that nano vesicles have a negative charge, whereas when the surface of nano vesicles is coated with plasma, the positive ions increase and become neutral.

FIG. 4 is a graph showing the overtime effect of a plasma coating method according to an embodiment of the disclosure.

FIG. 4 enables to confirm the time-dependent stability of the zeta potential of the plasma-coated nanovesicles compared to the nanovesicles.

Referring to FIG. 4 above, it is possible to confirm that nanovesicles do not have a change in a negative voltage, and plasma-coated nanovesicles gradually change to a more negative voltage after 12 hours.

At this time, it is possible to confirm that the nanovesicles of the disclosure have a positive charge when the plasma coating time is 12 hours or longer.

FIG. 5 is an exemplary diagram showing the improved cell affinity characteristics of a plasma coating method according to an embodiment of the disclosure.

FIG. 5 shows a representative 3D-RI cross-sectional image of plasma-coated nanovesicles fluorescently labeled with anticancer drug doxorubicin compared to nanovesicles.

FIG. 5 shows the intracellular penetration characteristics, wherein it is possible to confirm that nanovesicles do not deliver a drug well, as the relative fluorescence value of anticancer drug doxorubicin is 0.06 at 45 minutes and 0.24 at 90 minutes, and in the case of plasma coating, the permeability increases significantly to 0.33 at 45 minutes and 0.79 at 90 minutes, resulting in well delivery of a drug.

The above description of the disclosure is for illustrative purposes, and those skilled in the art will understand that it can be easily modified into other specific forms without changing the technical idea or essential features of the disclosure. Therefore, it should be understood that the embodiments described above are exemplary in all respects and not limiting. For example, each component described as a single type may be implemented in a distributed manner, and likewise, components described as distributed may be implemented in a combined form.

The scope of the disclosure is indicated by the following claims, and all changes or modified forms derived from the meaning and scope of the claims and their equivalent concepts should be interpreted as being included in the scope of the disclosure.

EXPLANATION OF REFERENCE NUMERALS

10: Plasma source device
20: First electrode
30: Second electrode
40: Plasma power device
50: Gas input device
60: Chamber
100: Nanovesicle
200: Positive charge

What is claimed is:

1. A method for plasma coating on a nanovesicle surface, comprising:

preparing a mixture by dissolving nanovesicles in a phosphate buffered saline (PBS) solution;

injecting the mixture containing the nanovesicles into a plasma jet device; and applying a preset voltage to the plasma jet device and performing plasma coating on the surface of the nanovesicles under preset gas flow conditions.

2. The method of claim 1, wherein in the performing of the plasma coating on the surface of the nanovesicles, the charge on the surface of the nanovesicles is converted from negative to neutral.

3. The method of claim 1, wherein in the preparing of the mixture, the content of the nanovesicles in the mixture is 1 wt % to 99.99 wt % of the total mixture.

4. The method of claim 1, wherein in the preparing of the mixture, the concentration of the PBS solution in the mixture is 0.001 M to 1 M.

5. The method of claim 1, wherein in the performing of the plasma coating on the surface of the nanovesicles, the applied voltage for generating plasma is 1 kW to 50 kW.

6. The method of claim 1, wherein in the performing of the plasma coating on the surface of the nanovesicles, an applied frequency for generating plasma is 1 kHz to 100 kHz.

7. The method of claim 1, wherein in the performing of the plasma coating on the surface of the nanovesicles, the flow rate of gas applied in the plasma coating process is 1 ccm/min to 50 ccm/min.

* * * * *